United States Patent [19]
Uram

[11] Patent Number: 5,409,480
[45] Date of Patent: Apr. 25, 1995

[54] LASER ENDOSCOPE SYSTEM CONSOLE

[76] Inventor: Martin Uram, 39 Sycamore Ave., Little Silver, N.J. 07739

[21] Appl. No.: 116,283

[22] Filed: Sep. 3, 1993

Related U.S. Application Data

[63] Continuation-in-part of Ser. No. 17,847, Feb. 16, 1993, abandoned.

[51] Int. Cl.⁶ .............................................. A61N 5/06
[52] U.S. Cl. ........................................ 606/10; 128/4; 128/6; 607/89; 362/259; 362/294; 362/373
[58] Field of Search ........................................ 606/1–4, 606/10–12; 362/259–265, 294, 373; 128/4, 6; 607/89

[56] References Cited

U.S. PATENT DOCUMENTS

| | | | |
|---|---|---|---|
| 5,072,338 | 12/1991 | Hug et al. | 362/373 |
| 5,131,382 | 7/1992 | Meyer | 128/6 |

Primary Examiner—Peter A. Aschenbrenner
Assistant Examiner—Michael Peffley
Attorney, Agent, or Firm—McAulay Fisher Nissen Goldberg & Kiel

[57] ABSTRACT

An endoscope laser system console including a chassis having a front wall, a rear wall, and a first side wall connecting the front and rear walls; an interior wall connected to the rear wall and positioned substantially perpendicular to the rear wall, the interior wall extending forward to approximately midway between the front and rear walls, a first rear channel zone on a first side of said interior wall, a second rear channel zone on a second side of said interior wall, and a front area zone in communication with the first and second rear channel zones; a laser assembly positioned within the first rear channel zones; a system electronics assembly positioned within the second rear channel zone; a lamp assembly positioned within the front area zone; a camera assembly positioned within the front area between the front wall and the lamp assembly; an intake fan mounted on the rear wall for supplying air into the first rear channel zone over the laser assembly; an exhaust fan mounted on the rear wall for forcing air from the second rear channel zone over the system electronics assembly; and, an intermediate fan, positioned within the front area zone for guiding air from the front area, over the lamp assembly, and out of the chassis through an exhaust port in the first side wall.

6 Claims, 2 Drawing Sheets

LASER ENDOSCOPE SYSTEM CONSOLE

This is a continuation-in-part application of Ser. No. 08/017,847, filed Feb. 16, 1993, now abandoned.

BACKGROUND OF THE INVENTION

This invention relates to a surgical endoscope laser system console for use in surgical procedures.

Recent developments in ophthalmologic surgical technology have made it possible to manufacture an endoscope probe for supplying illumination to, receiving visual images from, and providing laser energy to the area being operated upon. Additional procedures including aspiration and irrigation may also be performed using the endoscope probes.

A laser endoscope probe of this nature is disclosed in U.S. Pat. No. 5,121,740, issued to Martin Uram on Jun. 16, 1992.

A laser endoscope requires the following support components: a laser source, a light source, imaging lenses and monitor, and supporting electronics for each of the components. Each of these components is currently available, however, each component has its own chassis, support electronics, and cooling system.

One of the problems encountered by an arrangement having individual components is that a relatively large amount of space is required to provide for each of these components. Furthermore, the need to provide the surgeon with access to controls for each of the individual components, requires that the numerous components be positioned in the operating area, within the surgeons reach. Co-pending U.S. Pat. application Ser. No. 08/017,847, filed Feb. 16, 1993, discloses a system control panel providing controls for a number of system parameters. The convenience of a combined system control panel is facilitated by a single chassis device. Merely removing the components from their individual chassis and placing them within a single chassis has resulted in many problems. More specifically, adverse effects due to the heat generated within a single chassis, as well as, electromagnetic interference, have hindered such a construction. While liquid cooling may be provided to minimize problems due to heat, providing liquid cooling both increases production costs and is very inconvenient. Typically, a liquid cooling system requires a storage tank, a circulator, a heat exchanger and liquid circulation tubing. These components are susceptible to corrosion, require maintenance, add to the system size and weight, and often reduce component accessibility, leading to an overall cumbersome design.

Accordingly, it is an objective of the present invention to provide a single chassis having each of the laser endoscope supporting components therein. It is a further objective of the present invention to minimize adverse effects due to heat and electromagnetic interference while providing for light beam and image focusing, as well as, providing convenient access to ports to connect external devices. A still further objective of the present invention is to properly cool the components without employing an expensive fluid cooling system.

An additional problem encountered by an arrangement having individual components is that inevitably, cables for connecting the components to the endoscope's probe, imaging equipment, and power sources will be draped around the operating area, resulting in an increased risk of injury. In addition, set-up time for a surgical operation employing a laser endoscope probe and individual components is extensive. The set-up time is increased if safety measures are taken to secure cables to prevent accidents.

Accordingly, it is a further objective of the present invention to provide a portable, convenient, and easily assembled laser endoscope system.

BRIEF DESCRIPTION

A first embodiment of the laser endoscope system console of the present invention comprises a chassis having an interior wall, a laser assembly, system electronics, a lamp assembly, a camera assembly and a series of fans.

The console of this invention provides an optimum trade-off between the following factors: (a) the proper light source which minimizes light losses and enables illumination and viewing; (b) maximizing heat dissipation of the laser assembly, lamp assembly, and system electronics; (c) minimizing adverse effects due to heat generated within the console on the individual assemblies; (d) minimizing electromagnetic interference; (e) minimizing costs, especially with respect to the cooling system; (f) conveniently positioning connecting ports; and (g) minimizing the size of the console chassis.

The laser within the laser assembly generates a substantial amount of heat. Provisions must be made for dissipating the heat generated by the laser to prevent the laser from overheating. Similarly, the lamp within the lamp assembly also generates heat. Accordingly, dissipation of the lamp heat is also required to prevent the lamp from overheating.

Both the camera assembly and the system electronics are heat sensitive. If exposed to high heat, they yield unpredictable results. Accordingly, the camera assembly and the electronics system must be protected from the heat dissipated by the laser and lamp assemblies.

In addition to generating heat, the laser and lamp assemblies generate electromagnetic energy. The system electronics, being sensitive to electromagnetic energy, must be protected from the electromagnetic energy generated within the console.

The connections for supplying light from the lamp to the illumination guide, laser energy to the laser guide, and a video image to the camera assembly are positioned on one side panel of the chassis.

BRIEF DESCRIPTION OF THE DRAWINGS

FIG. 2 is a view along the line 2—2 in FIG. 1.

FIG. 3 is a view from the back of the console and shows only the system electronics assembly at the upper rear portion of FIG. 1.

DETAILED DESCRIPTION OF THE PREFERRED EMBODIMENT

Figure 1:
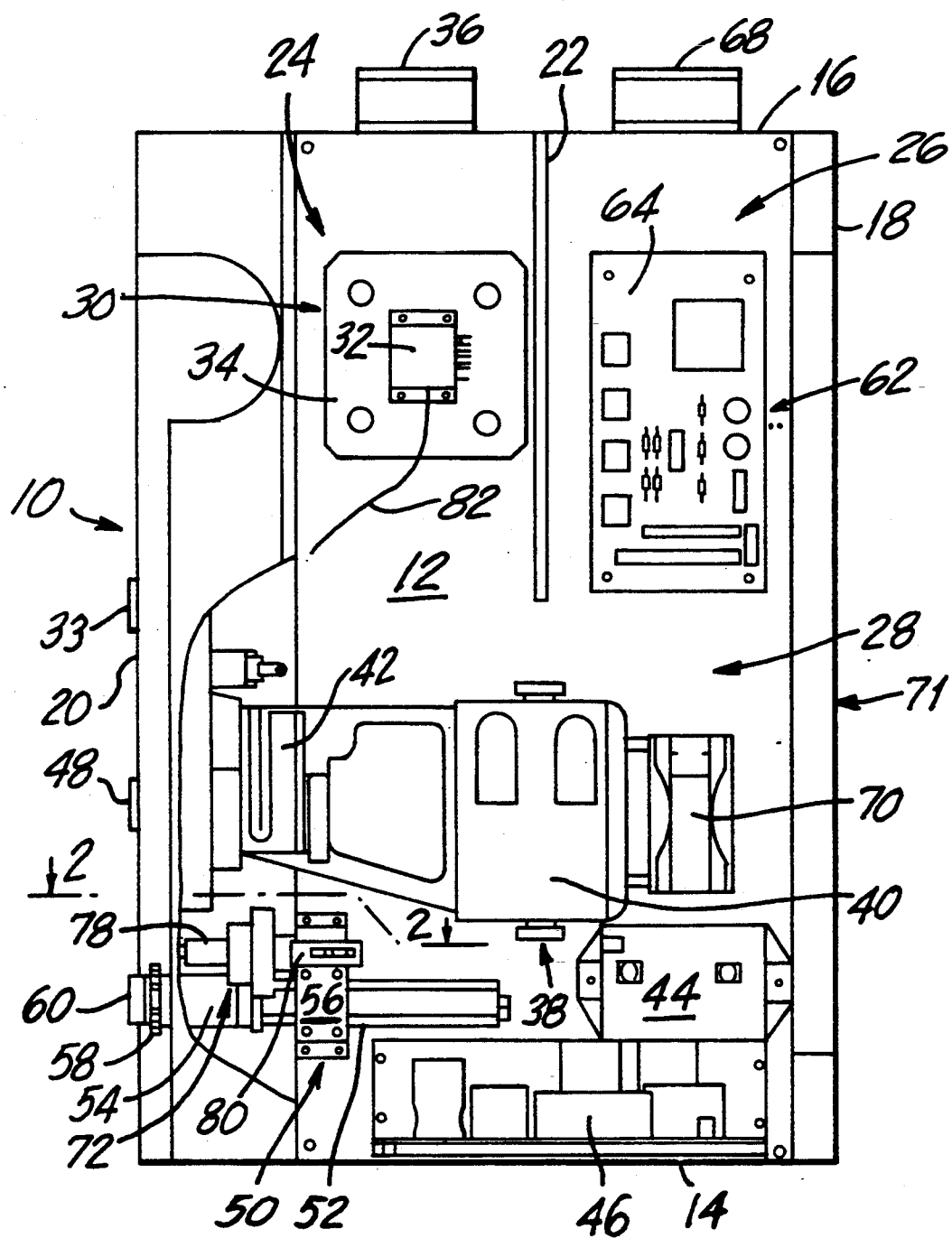
FIG. 1 is an elevated view of the arrangement of the components within a laser endoscope system console.

Referring to FIG. 1, laser endoscope system console 10 comprises chassis 12 having front wall 14, rear wall 16 and side walls 18, 20. Interior wall 22 protrudes into chassis 12 and defines two rear channel zones 24, 26 and front area zone 28.

Laser assembly 30 comprises diode laser 32 mounted upon heat sink 34. Preferably, diode laser 32 has an operating wavelength of 810 nm. Diode laser 32 is connected to second port 33. Second port 33 is adapted to couple laser energy provided by laser assembly 30 to a laser guide of an endoscope laser probe. Heat sink 34 operates to dissipate heat generated by diode laser 32 in a known fashion. Intake fan 36 is mounted over an opening in rear wall 16. Intake fan 36 operates to supply air into rear channel zone 24. The air supplied by intake fan 36 is forced into rear channel zone 24 to facilitate heat dissipation from laser assembly 30.

Lamp assembly 38 comprises xenon lamp 40 and optics assembly 42. Preferably, xenon lamp 40 has a color temperature of approximately 5700° K. Lamp ignitor 44, and power supply 46 are connected to lamp assembly 38. Lamp assembly 38 is mounted in front area zone 28 on bracket 47. Lamp 40 is positioned so that the focal point of lamp 40 occurs at illumination port 48. Positioning the focal point at illumination port 48 causes a focused light beam to be supplied to the illumination guide of a laser endoscope attached at illumination port 48.

Camera assembly 50 comprises video camera 52 and video lens 54. Camera assembly 50 is mounted in front area zone 28 on camera mount 56. Camera assembly 50 is positioned between front wall 14 and lamp assembly 38. Video lens 54 is positioned to protrude from side wall 20 so that camera focus 58 may be manually adjusted from outside chassis 12.

Receiving end 60 of video lens 54 receives an imaging guide of an endoscope and couples the imaging guide to video camera 52. As a result, the area being operated upon with the endoscope may be viewed using a video monitor (not shown) connected to video camera 52.

Preferably, the distance between laser assembly 30 and lamp assembly 38 is greater than the distance between lamp assembly 38 and camera assembly 50.

Figure 3:
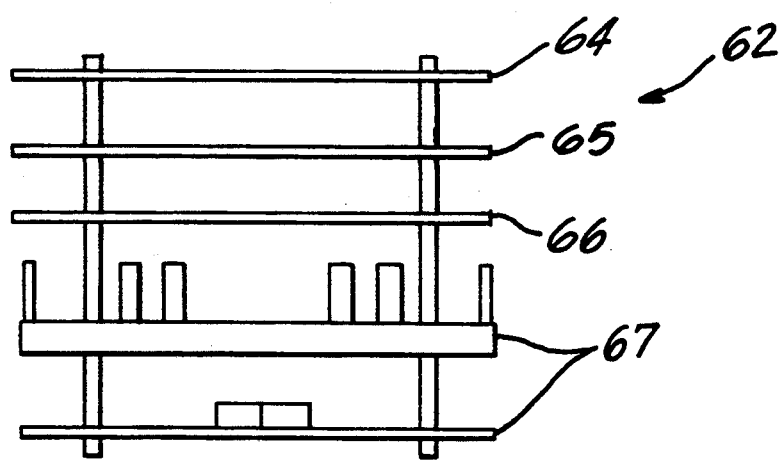
FIG. 3 is a side view of the stack of boards that constitute the system electronics assembly 62 of the FIG. 1 embodiment.

Referring to FIG. 3, system electronics assembly 62 comprises interface PC board 64, CPU PC board 65, aiming beam board 66 and laser driver assembly 67. PC boards 64, 65, 66 and laser driver assembly 67 are stacked within rear channel zone 26 and separated by stand-offs. Preferably, system electronics assembly 62 has a total height of approximately 5.5 inches.

Interior wall 22 shields system electronics assembly 62 from electromagnetic energy produced by laser assembly 30. Interior wall 22 also provides some protection to system electronics assembly 62 from the heat dissipated by laser assembly 30.

Exhaust fan 68 is mounted over an opening in rear wall 16. Exhaust fan 68 operates to force air out of rear channel zone 26. Exhaust fan 68 pulls air into rear channel zone 26 and then expels the air from chassis 12. The air flow through rear channel zone 26, facilitates heat dissipation from system electronics assembly 62. Operation of intake fan 36 and exhaust fan 68 causes air to flow through intake fan 36, into rear channel zone 24, over laser assembly 30, into front area zone 28, into rear channel zone 26, over system electronics assembly 62, and through exhaust fan 68.

Intermediate fan 70 is positioned within front area zone 28 to force air from front area zone 28, over lamp assembly 38, and out of chassis 12 through vent 71 to facilitate heat dissipation from lamp assembly 38. Intermediate fan 70 may be directly attached to lamp assembly 38.

The primary air flow patterns serve two important functions: first, the heat generated by laser assembly 30, lamp assembly 38, and system electronics assembly 62 is dissipated quickly due to the specified air flow patterns; and second, the primary air flow patterns directs the heat dissipated by the three components away from heat sensitive camera assembly 50. The air flow patterns within the present invention are made possible due to interior wall 22, intake fan 36, intermediate fan 70, exhaust fan 68, and vent 71.

Figure 2:
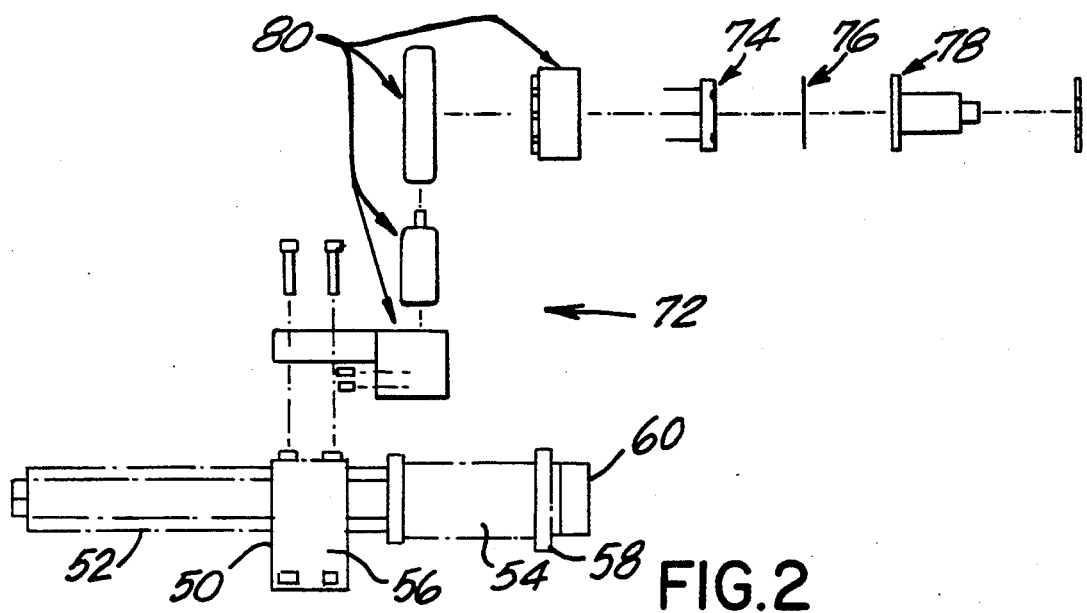
FIG. 2 is an exploded side view of the laser power meter assembly 72 which is shown in assembled form in the lower left portion of FIG. 1.

Referring to FIG. 2, laser power meter assembly 72 comprises power meter detector 74, power meter filter 76, and power meter probe adapter 78. Power meter assembly is mounted on camera mount 56 using mounting assembly 80.

Laser power meter assembly 72 is designed to allow the tip of a laser endoscope to be inserted into power meter probe adaptor 78, so that the laser power emitted from the laser endoscope may be measured. The laser power meter is interfaced to the interface PC board 64 via an electrical cable assembly. An electrical signal from laser power meter assembly 72 is processed by CPU board 65.

A laser power display for indicating the laser power selected by the user may also be provided. While the system is in the calibration mode, however, the laser power display displays the laser power measured by laser power meter assembly 72.

Preferably, illumination port 48, video port 60, and power meter probe adapter 78 are positioned in the front half of side wall 20.

What is claimed is:

1. An endoscope laser system console comprising:
   a chassis having a front wall, a rear wall, and a first side wall connecting said front and rear walls;
   an interior wall connected to said rear wall and positioned substantially perpendicular to said rear wall, said interior wall extending forward to approximately midway between said front and rear walls, a first rear channel zone on a first side of said interior wall, a second rear channel zone on a second side of said interior wall, and a front area zone in communication with said first and second rear channel zones,
   a laser assembly positioned within said first rear channel zone;
   a system electronics assembly positioned within said second rear channel zone;
   a lamp assembly positioned within said front area zone;
   a camera assembly positioned within said from area zone between said from wall and said lamp assembly;
   an intake fan mounted on said rear wall for supplying air into said first rear channel zone over said laser assembly;
   an exhaust fan mounted on said rear wall for forcing air from said second rear channel zone over said system electronics assembly; and,
   an intermediate fan, positioned within said front area zone for guiding air from said front area zone, over said lamp assembly, and out of said chassis through an exhaust port in said first side wall.

2. The endoscope laser system console of claim 1, said lamp assembly being positioned a first distance from said laser assembly and a second distance from said camera assembly, said first distance being larger than said second distance.

3. The endoscope laser system console of claim 1, said chassis having a second side wall connecting said front and rear walls, wherein:
- a first port is provided in said second side wall, said first port being in optical communication with said lamp assembly and adapted to couple an illumination guide of an endoscope to light provided by said lamp assembly;
- a second port is provided in said second sidewall, said second port being in optical communication with said laser assembly and adapted to couple a laser guide of an endoscope laser probe to laser energy provided by said laser assembly; and,
- a third port is provided in said second sidewall, said third port being in optical communication with said camera assembly and adapted to couple an image provided by an imaging guide of an endoscope to said camera assembly.

4. The endoscope laser system console of claim 3 wherein said first, second and third ports are positioned in a front portion of said second side wall.

5. The endoscope laser system console of claim 1 wherein said lamp assembly comprises a xenon lamp having a color temperature of approximately 5700° K.

6. The endoscope laser system of claim 1 wherein said laser assembly comprises a diode laser mounted on a heat sink.

* * * * *